United States Patent
Filippi et al.

(10) Patent No.: US 8,721,975 B2
(45) Date of Patent: May 13, 2014

(54) PLANT FOR UREA PRODUCTION

(75) Inventors: Ermanno Filippi, Castagnola (CH);
Enrico Rizzi, Casnate con Bernate (IT);
Mirco Tarozzo, Ligornetto (CH);
Federico Zardi, Breganzona (CH)

(73) Assignee: Urea Casale SA (CH)

( * ) Notice: Subject to any disclaimer, the term of this patent is extended or adjusted under 35 U.S.C. 154(b) by 0 days.

(21) Appl. No.: 12/367,240

(22) Filed: Feb. 6, 2009

(65) Prior Publication Data

US 2009/0220396 A1  Sep. 3, 2009

Related U.S. Application Data

(63) Continuation of application No. 10/519,742, filed as application No. PCT/EP03/05839 on Jun. 4, 2003, now abandoned.

(30) Foreign Application Priority Data

Jun. 28, 2002 (EP) .................................. 02014473

(51) Int. Cl.
| | | |
|---|---|---|
| *C01C 1/00* | (2006.01) | |
| *B01J 8/00* | (2006.01) | |
| *B01J 19/00* | (2006.01) | |
| *F28D 7/00* | (2006.01) | |
| *B01J 19/24* | (2006.01) | |
| *B01D 5/00* | (2006.01) | |
| *F28D 7/02* | (2006.01) | |
| *F28D 7/10* | (2006.01) | |
| *C07C 273/00* | (2006.01) | |

(52) U.S. Cl.
USPC ........... 422/148; 422/129; 422/149; 422/187; 422/198; 422/200; 422/201; 422/600; 422/608; 422/614; 564/67; 564/70; 564/72; 165/157; 165/158; 165/159; 165/160; 165/161; 165/162; 165/163

(58) Field of Classification Search
USPC ......... 422/148, 200, 201, 208, 189, 149, 600, 422/608, 614, 198, 129, 187; 564/67, 70, 564/72; 165/157–163, 168–170, 177
See application file for complete search history.

(56) References Cited

U.S. PATENT DOCUMENTS

| | | | | |
|---|---|---|---|---|
| 888,169 | A | | 5/1908 | Heizmann |
| 3,294,082 | A | * | 12/1966 | Norris ........................ 126/116 R |
| 3,512,239 | A | | 5/1970 | Rosenblad |

(Continued)

FOREIGN PATENT DOCUMENTS

| | | | |
|---|---|---|---|
| EP | 1153653 A1 | * | 11/2001 |
| WO | 00/43358 A1 | | 7/2000 |
| WO | WO 02/090323 | * | 11/2002 |

OTHER PUBLICATIONS

Reppich, M. "Use of High Performance Plate Heat Exchangers in Chemical and Process Industries", Int. J. Therm. Sci., 1999, vol. 38, pp. 999-1008.

(Continued)

*Primary Examiner* — Natasha Young
(74) *Attorney, Agent, or Firm* — Akerman LLP

(57) ABSTRACT

Plant for urea production from ammonia and carbon dioxide having a so-called high-pressure section which comprises a synthesis reactor and a condensation unit (7, 107) positioned inside the reactor, all substantially operating at the same pressure.

2 Claims, 7 Drawing Sheets

(56) References Cited

U.S. PATENT DOCUMENTS

| | | |
|---|---|---|
| 4,519,446 A | 5/1985 | Elmore et al. |
| 5,507,356 A * | 4/1996 | Roth et al. .................... 165/111 |
| 2001/0045276 A1 | 11/2001 | Ohashi |
| 2002/0004612 A1* | 1/2002 | Fukunaka et al. .............. 564/67 |
| 2002/0088613 A1* | 7/2002 | Filippi et al. .................. 165/182 |

OTHER PUBLICATIONS

Rohsenow, W. et al. "Handbook of Heat Transfer", McGraw-Hill, Third Edition, 1998, pp. 17.22-17.28.

* cited by examiner ll # PLANT FOR UREA PRODUCTION

FIELD OF APPLICATION

In its most general aspect the present invention refers to a so-called "urea stripping plant" for producing urea from ammonia and carbon dioxide.

More specifically, this invention concerns the high-pressure section of a plant of the aforementioned type comprising a urea synthesis reactor and a condenser or else a urea synthesis reactor, a stripper and a condenser.

PRIOR ART

From the main reaction between ammonia and carbon dioxide, carried out in certain well-known pressure and temperature conditions, an aqueous solution comprising urea, ammonium carbamate and free ammonia (i.e. not bound with the carbamate) and a gaseous mixture comprising ammonia, carbon dioxide, water (in steam phase), plus possible inert gases are obtained.

In processes that use so-called stripping technology, the aqueous solution containing urea (product of the reaction) that comes out of the synthesis reactor is subjected, in an appropriate stripper, to a heat treatment for the decomposition of the carbamate in ammonia and carbon dioxide and simultaneously to stripping (for example through the same flow of carbon dioxide fed to the urea plant) to separate a flow of gas comprising most of the unreacted ammonia and carbon dioxide from said solution.

These gases, to which one adds the carbon dioxide used for stripping, are recondensed to carbamate in an appropriate condenser (known as high-pressure carbamate condenser) and the carbamate is recycled in the synthesis reactor.

Also the ammonia and carbon dioxide present in gas phase in the reaction mixture coming out from the reactor, are generally transformed into ammonium carbamate, in particular through absorption in an appropriate condenser (known as a scrubber) with the help of a flow of carbamate coming from the urea recovery section. The flow of carbamate coming out from said scrubber is recycled, via the high-pressure carbamate condenser, to the synthesis reactor.

In the plants for urea production considered here (Urea Stripping Plant—USP), synthesis reactor, stripper, condenser and scrubber all operate substantially at the same pressure (high-pressure) and constitute the most important elements of the so-called "high-pressure section" of such plants.

In the prior art of the sector, it has advantageously been proposed to comprise in the same shell (high-pressure vessel) of the synthesis reactor also one or both of the other functions of (high-pressure) carbamate condenser and scrubber. For example in WO 00/43358 (PCT/NL/00044), included here for reference, a synthesis reactor is described in the vertical shell of which a reactor section is defined between a condenser section lying below it, and a scrubber section lying above it; the scrubber and condenser sections are in fluid communication through a vertical duct which crosses the entire reactor section and which is used to feed said condenser with the entire flow of carbamate formed in the scrubber itself.

Although advantageous under different aspects, the aforementioned plants for urea production of the prior art have some drawbacks as yet not overcome.

A first and most substantial drawback consists of a recognised upper limit of productive capacity, which is practically not overcome, to the point that, to obtain substantial productions, it is necessary to install one or more other similar plants (many lines, double apparatuses).

Indeed, in the plants of the prior art, and with particular reference to their high-pressure section, the condenser and the stripper essentially consist of respective heat exchange units exclusively formed from tube bundles, in which the tubes, in general, connect to opposite tubular support plates, said tubes being internally crossed, respectively, by the gases to be condensed and by the aqueous solution comprising carbamate to decompose and to subject to stripping.

The tubular plates are designed directly according to the number of tubes to be supported. The degree of the heat exchange that can be obtained in the condenser and in the stripper and, therefore, the "productive capacity" of both the condenser and of the stripper depends upon the number of tubes and upon their size. Consequently, it can be said that the productive capacity that one intends to obtain from a plant of the type considered, or rather from its high-pressure section, depends also upon the number and the size of the tubes of the tube bundles (and therefore upon the size of the relative tubular plates) used in the condenser and in the stripper of such section. Therefore, it can be said that said tubular plates must be realised with a size (diameter), thickness and weight which gradually increase as the productive capacity of said high-pressure section increases.

There are recognisedly sizes and weight of the tubular plates beyond which it is no longer economically viable nor technically possible to position them inside a pressure vessel of, for example, a conventional urea synthesis reactor, or of a condenser or of a stripper. This gives the upper limit of the productive capacity of the plants of the prior art.

Another drawback of the use of tube bundles consists of the difficulty of distributing the fluid inside each tube and of guaranteeing that each tube be appropriately cooled or heated by the operating fluid which acts outside of it.

The last but not least drawback consists of the long times in which the plant is inoperative required to identify and replace tubes which may be damaged, for example by corrosion, as well the drawbacks of the constructive difficulties and the high costs for realising such reactors.

SUMMARY OF THE INVENTION

The problem forming the basis of the present invention is that of providing a plant for urea production, of the type known as a "urea stripping plant" in which the functional components of its high-pressure section have structural and functional characteristics such as to overcome the aforementioned drawbacks with reference to the prior art, with particular reference to the limitation in productive capacity.

This problem is solved according to the present invention by a plant of the aforementioned type the high-pressure section of which comprises a synthesis reactor, a condensation unit positioned inside said reactor, a stripper and a scrubber, all operating substantially at the same pressure, having the structural characteristics specified in the subsequent claims.

DETAILED DESCRIPTION

Figure 1:
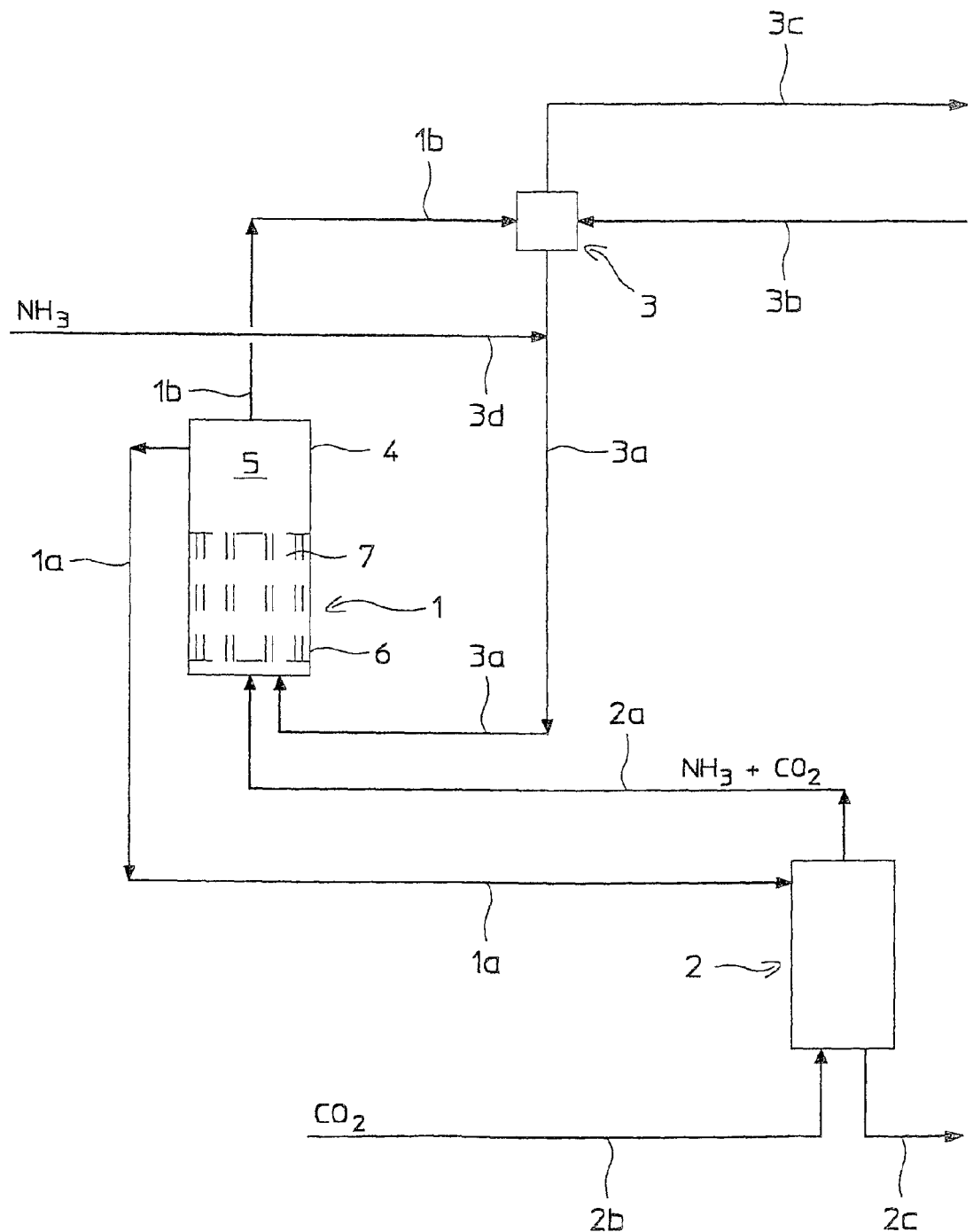
FIG. 1 represents a schematic view of the high-pressure section of a plant for urea production according to the present invention.

With reference to FIG. 1, the high-pressure section of a plant for urea production from ammonia and carbon dioxide, of the type known as a "urea stripping plant", essentially comprises a synthesis reactor 1, a stripper 2 and a scrubber 3, all operating at the same pressure.

In the vertical shell 4 of said synthesis reactor 1, an actual reactor zone 5 and a condensation zone 6 are defined, in which a condensation unit 7, which shall be described in detail hereafter, is supported.

In the reactor zone 5 suitable perforated plates, which are per se known since they are conventional, can be provided for, represented with a broken line in FIG. 1 with reference numeral 5a.

In accordance with a non-limiting example of urea production through the aforementioned plant, the aqueous solution produced in the reactor 1, essentially comprising urea, ammonium carbamate and free ammonia, is sent, through duct 1a, to the stripper 2, fed, at the same time, from below, through duct 2b, with a current of carbon dioxide (corresponding to the carbon dioxide fed to the plant or to part of it).

The gases coming out from the stripper 2, essentially carbon dioxide and ammonia, are sent, through the duct 2a, to the reactor 1, entering below the condensation unit 7.

The solution coming out from the stripper 2, essentially a urea, ammonium carbamate and free ammonia solution, is sent, through duct 2c, to the urea recovery section (not represented).

The gases coming out from the synthesis reactor 1, essentially unreacted ammonia and carbon dioxide and possible inert gases, are fed through duct 1b, to the scrubber 3 where, freed from the inert gases (duct 3c) they are condensed with the help of a flow of carbamate coming, through duct 3b, from the urea recovery section.

Coming out from the scrubber 3, the carbamate solution, with the ammonia necessary for the reaction added (duct 3d), is sent, through duct 3a, to the synthesis reactor 1, below said condensation unit 7.

Figure 2:
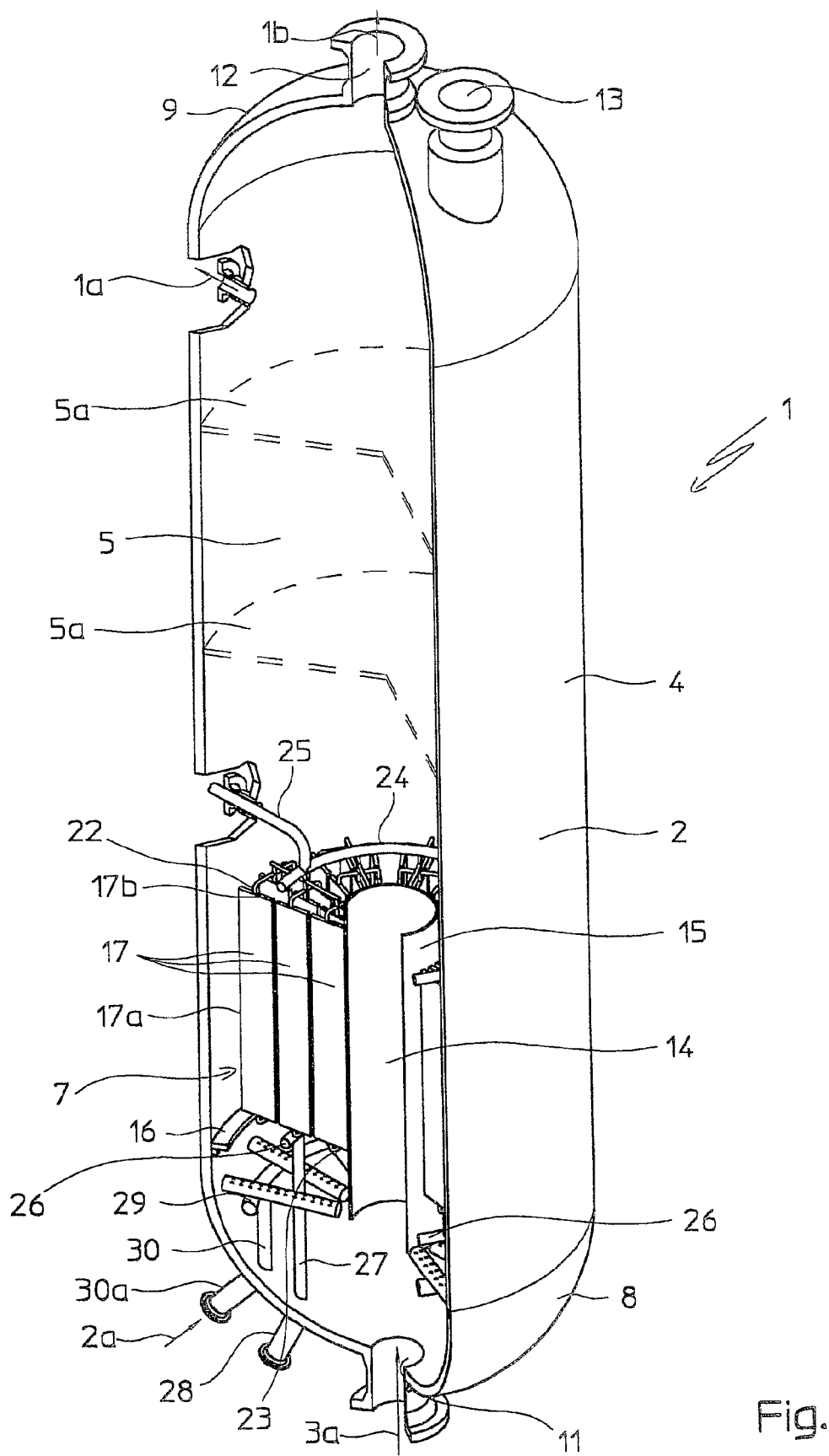
FIG. 2 represents an enlarged schematic view of the urea synthesis reactor of the plant of FIG. 1.

With reference to FIG. 2, the cylindrical shell 4 of said reactor 1 is closed at the opposite ends by respective base plates, lower 8 and upper 9; the base plate 8 is equipped with a connector or inlet port 3a, for the entry of the gases coming from the stripper 2 (as described hereafter) and with an axial passage 11, for the entry of the ammonia-carbamate mixture, coming from the scrubber 3, through the duct 3a. The base plate 9 is equipped with an axial passage 12 for discharging the gases produced by the reaction and with a manhole 13.

Said condensation unit 7 has an overall cylindrical annular configuration, coaxial with the shell 4. It has an outer diameter of a little less than the inner diameter of the shell 4 and is axially crossed by a passage 14, in which an axial duct 15 is removably mounted. Said duct 15 has preferably an axial length greater than that of said condensation unit 7, so as to protrude from both sides of it.

In a totally schematic way, the condensation unit 7 is supported by an annular bracket 16, fixed to the inner wall of the shell 4, at a predetermined distance from its base plate 8.

In accordance with the present invention, said condensation unit 7 comprises a plurality of plate-shaped heat exchange elements (or exchangers) 17, regularly distributed in many coaxial and concentric rows (three in the example); each exchanger 17 (FIG. 3) is substantially flattened box-shaped with an essentially elongated rectangle configuration, in which two opposite long sides 17a, 17a and two opposite short sides 17b, 17b are emphasized.

In the aforementioned condensation unit 7, the exchangers 17 are substantially arranged radially, with long sides 17a parallel to the axis of said unit 7 (and therefore to the axis of the shell 4), and short sides 17b, extending radially; they are also arranged to form pluralities of radial coplanar exchangers 17 in groups of three.

Obviously, according to different technical-applicational requirements, each radial group of three exchangers 17 can be replaced by a pair of coplanar plate-shaped exchangers, or by a single plate-shaped exchanger which substantially occupies the entire (annular) space between the axial duct 15 and the shell 4.

Yet more specifically (FIG. 3) each exchanger 17 consists of a pair of juxtaposed metallic plates 18, 19, reciprocally joined, in a predetermined spaced relationship, of perimetric welded joints so that a chamber 21 is defined between them, intended to be crossed by an operating heat exchange fluid.

Each exchanger 17 is equipped on opposite connector sides 22, 23 for the entry and exit, respectively, of said operating heat exchange fluid, into and from said chamber 21.

According to a first embodiment, the plates 18, 19 are mutually joined also through a plurality of welding points 18a, regularly distributed, for example, and preferably according to an arrangement in groups of five, which give the exchanger 17 a substantially "quilted" aspect. The presence of the welding points 18a is such that the crossing of the exchanger 17 by the operating heat exchange fluid takes place according to winding paths, with improve heat exchange efficiency.

The entry connectors 22 of the exchangers 17, are hydraulically connected to an annular distributor duct 24, supported in position lying over the condensation unit 7 and in turn in fluid communication with the outside of the reactor 1, through a duct 25, for feeding (or discharging) the predetermined heat exchange fluid.

The exit connectors 23, of the same exchangers 17 are hydraulically connected to an annular collector duct 26, supported below said unit 7 and in turn in fluid communication with the outside of the reactor 1, through a duct 27 and relative port 28, for discharging (or feeding) the operating heat exchange fluid.

Below the condensation unit 7, an annular tubular gas distributor 29 is supported in a conventional and non-represented manner, in fluid communication, through a duct 30 and relative port 30a, with the duct 2a in which the gases arrive from the stripper 2.

Figure 4:
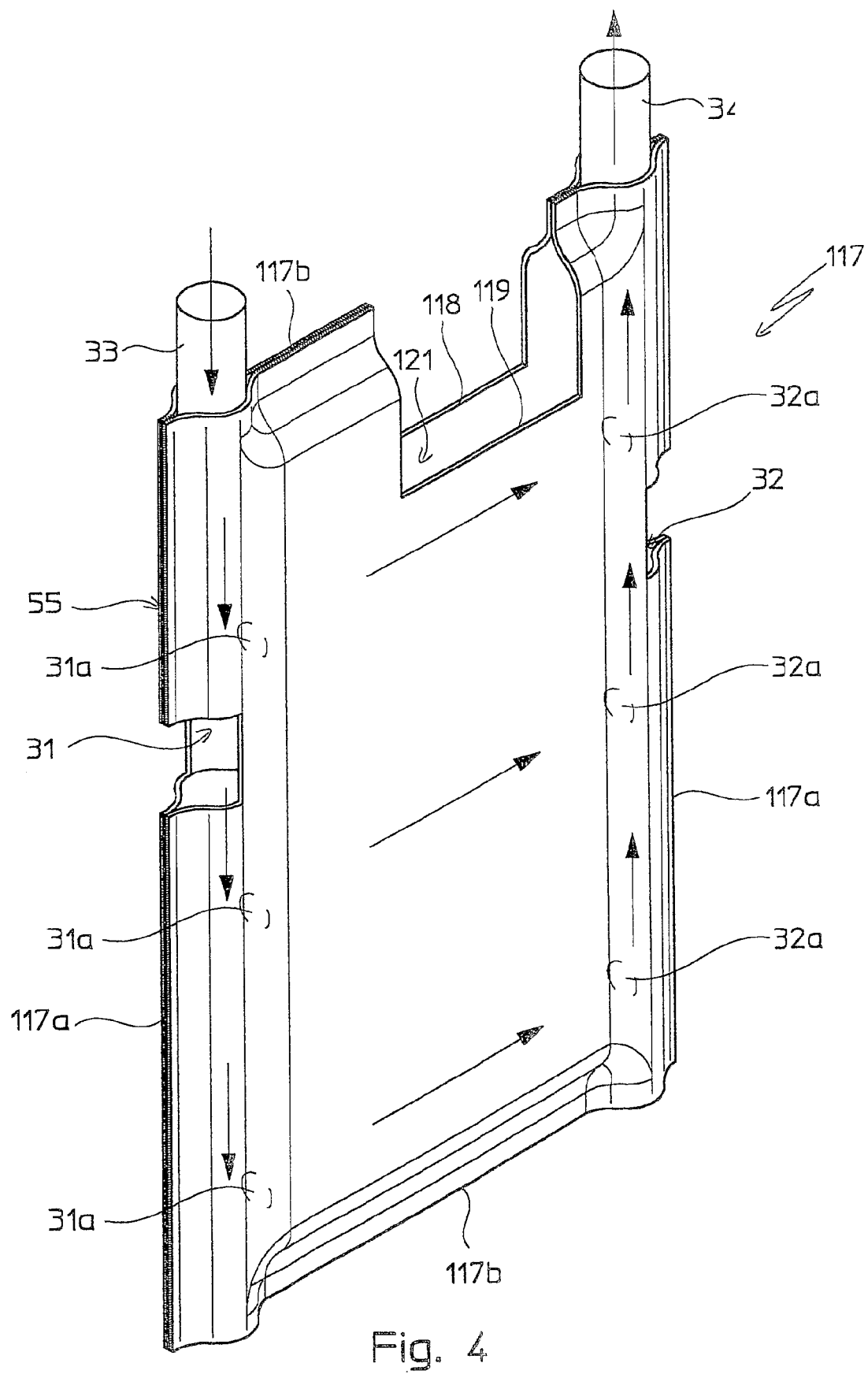
FIGS. 4 and 5 represent enlarged perspective and schematic views, respectively, of variant embodiments of the detail of FIG. 3.
Figure 5:
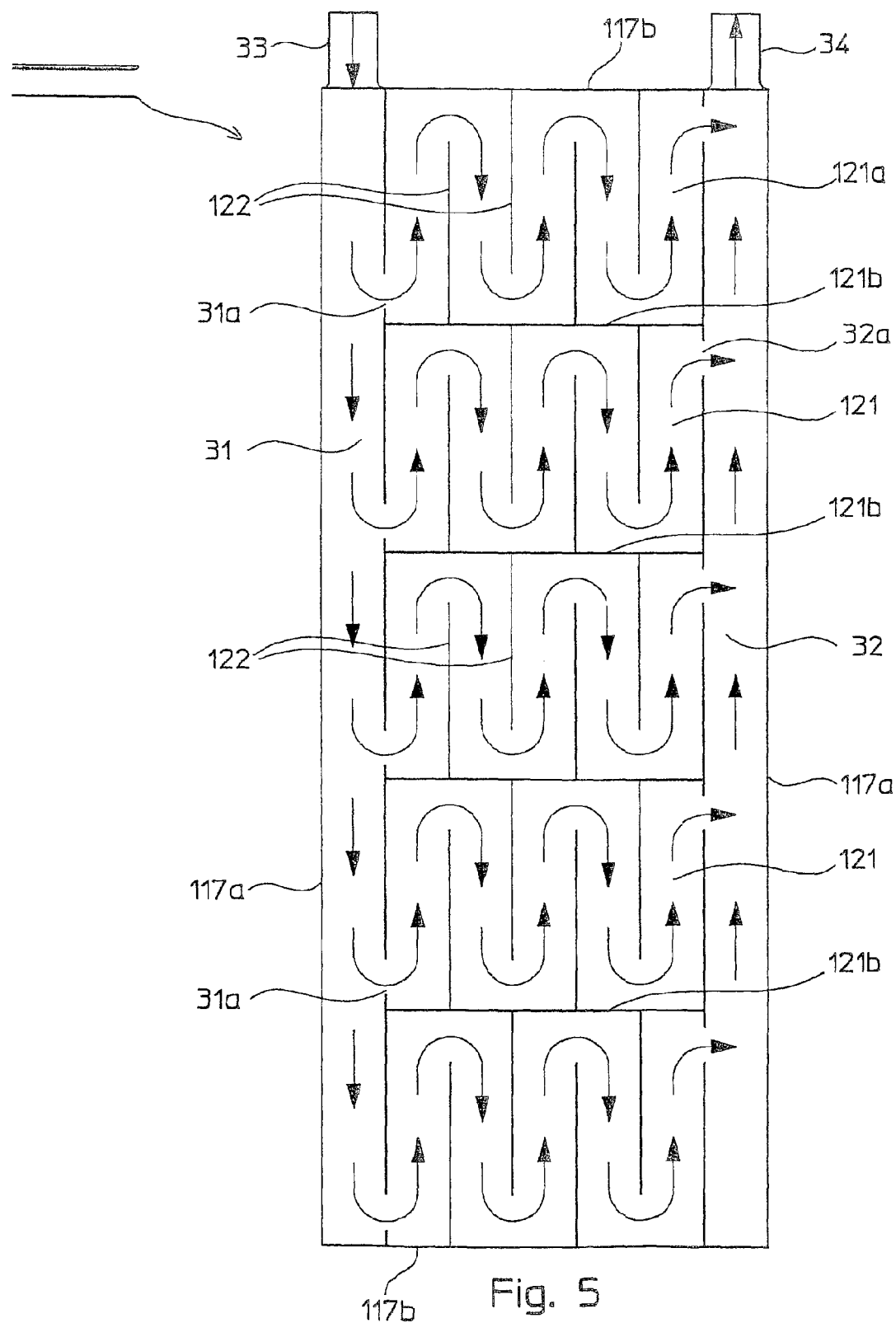

In FIGS. 4 and 5 a variant embodiment of the exchanger 17, intended to optimise the heat exchange efficiency, is represented.

According to this variant, each exchanger 117, still comprising a pair of juxtaposed plates 118, 119, mutually welded only perimetrically (thus without the "quilting" described above with reference to FIG. 3), is internally equipped, in correspondence with the opposite long sides 117a, with a distributor duct 31 and a duct 32 for collecting said heat exchange fluid, respectively. The ducts 31 and 32 are, on one side, in fluid communication with said chamber 121, through at least one, but preferably a plurality of openings or holes 31a and 32a, with which they are equipped along one or more generatrices and, on the other side, with the outside of the exchanger 117, through respective connectors 33 and 34, for the entry and exit of said operating fluid.

Said ducts 31 and 32 can be formed directly in the long sides 117a of the exchanger 117, at the time of the drawing and perimetric welding of the metallic plates 118 and 119, which constitute it, or else they can consist of respective tubes, fixed in said chamber 121, in correspondence with the long sides 117a, 117a of the exchanger and parallel to them. In this case, said tubes extend outside of the exchanger 117, to form a single piece with the respective connectors 33, 34, mentioned above.

In accordance with another characteristic of the aforementioned variant, the connectors 33, and 34 for entry and exit into and from each exchanger 117 are positioned in correspondence with the same short side 117b thereof.

When adapted to form a condensation unit having the arrangement described in FIG. 2, the short side 117b, with relative connectors 33 and 34, constitutes the upper side of each exchanger 117.

Advantageously, at least part of the exchangers 117, of the respective condensation unit, is realised according to the variant schematically illustrated in FIG. 5.

In this alternative embodiment, the inner chamber of each exchanger 117 is subdivided into a plurality of chambers 121a, not directly communicating with each other and obtained, for example, through a corresponding plurality of welding lines 121b of the metallic plates 118, 119, extending parallel to the short sides 117b of the exchanger 117, in other words perpendicular to its distributor and collector ducts 31, 32. Said chambers 121a, which can all have the same width or have different widths according to the requirements, are internally equipped with a plurality of deflector plates 122, extending parallel to said ducts 31, 32 and which define in each chamber 121a, a substantially coiled fluid path.

Each chamber 121a is in fluid communication with said distributor duct 31, through at least one opening 31a thereof and with said collector duct 32, through at least one opening 32a thereof.

It should be noted that, for an improved control of the pressure drops, and therefore of the distribution of the operating fluid inside the chambers 121a, the openings 31a of the distributor duct 31 are realised with a different width or diameter, in particular an increasing width in the flow direction of the operating fluid inside said duct 31.

Figure 6:
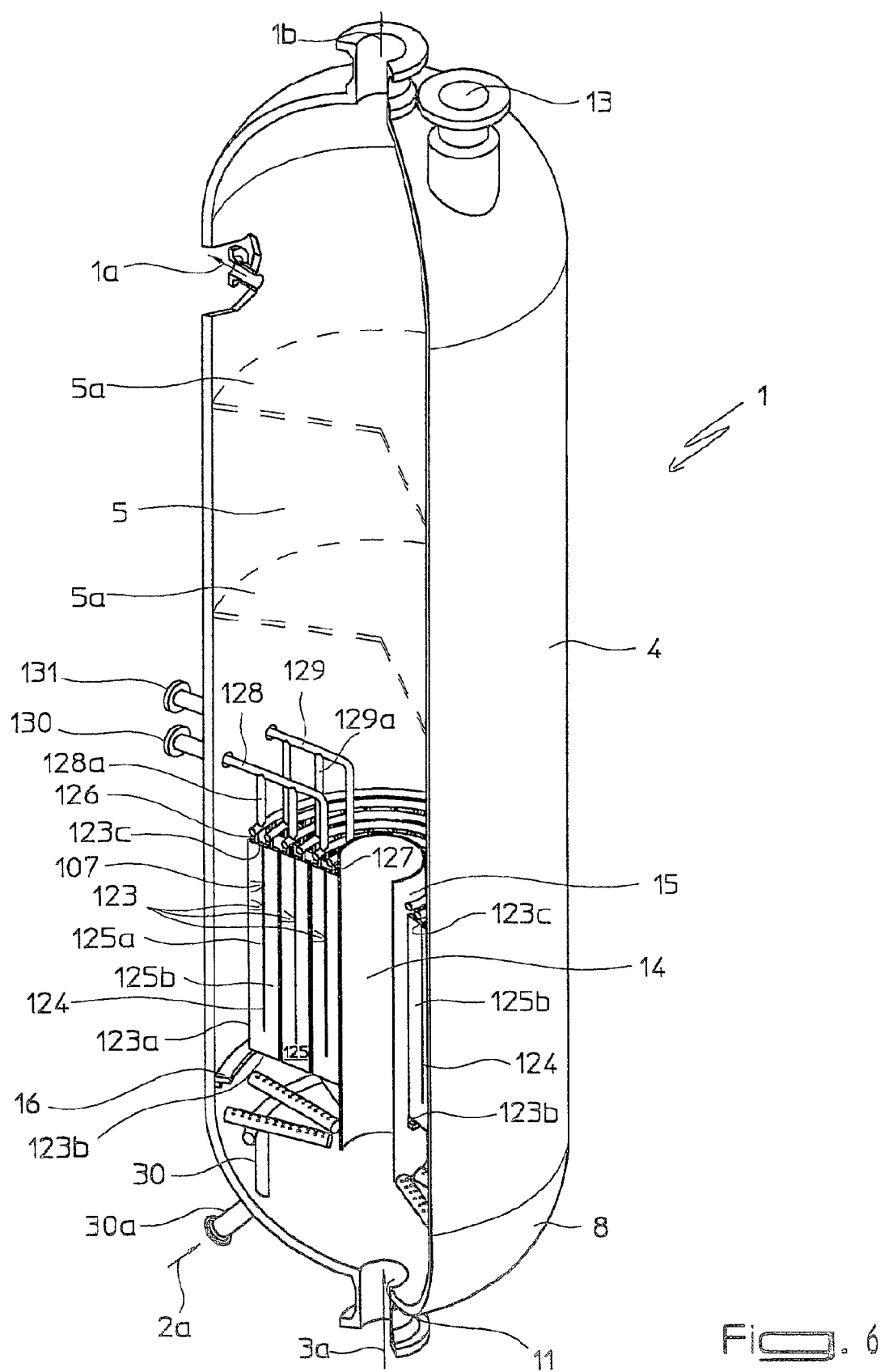
FIG. 6 represents a perspective partial section view of the reactor of FIG. 2 according to a further variant embodiment.

In FIG. 6 an enlarged view of a urea synthesis reactor 1 according to the finding is represented, equipped with a condensation unit 107, totally similar to the condensation unit 7 of the reactor of FIG. 2, but comprising heat exchange elements (or heat exchangers) 123 according to a further variant embodiment described hereafter.

In such a figure, the details of reactor 1, structurally and functionally equivalent to those described with reference to the reactor of FIG. 2, will be described with the same reference numeral and will not be further described.

In particular, according to this preferred but not limiting embodiment, schematised in FIG. 6, said condensation unit 107 comprises a plurality of heat exchangers 123, regularly distributed in three coaxial and concentric rows; each exchanger 123 has a substantially flattened box-shaped structure, with an essentially elongated rectangle configuration. According to the arrangement of FIG. 6, in the condensation unit 107, all of the exchangers 123 are arranged with long sides 123a parallel to the axis of the shell 4 and short sides 123b, 123c extending radially with respect to it.

Figure 3:
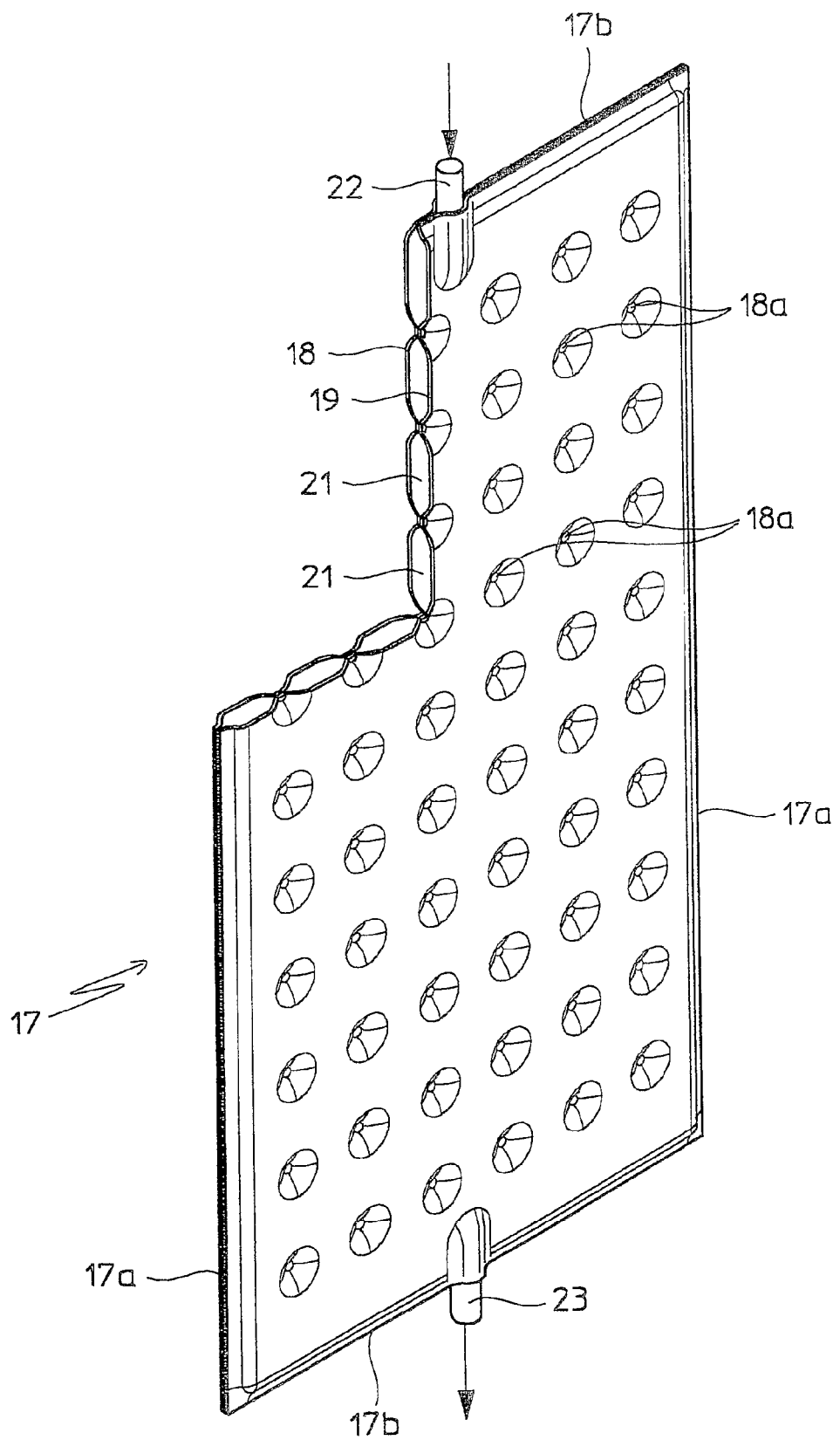
FIG. 3 represents a further enlarged perspective view of a detail of the synthesis reactor of FIG. 2.

Yet more precisely the exchangers 123 are of the type represented in FIG. 3, i.e. consisting of a pair of juxtaposed metallic plates, mutually joined, in a predetermined distanced relationship, through perimetric welding, so that between them a chamber 125 is defined, intended to be crossed by an operating heat exchange fluid.

In accordance with one characteristic of the present invention, inside each exchanger 123 a separator plate 124 is provided, extending from a short side 123c thereof and having a predetermined length which is shorter than that of the long sides 123a, extending in the same direction as these long sides 123a.

Preferably, the separator plate 124 is obtained through mutual welding of the two plates which form said exchanger 123, from a mid-point position of one of their short sides 123c and extending towards the opposite short side 123b, with respect to which it is in a predetermined spaced relationship.

Due to the presence of said separator plate 124, the aforementioned chamber 125 of each exchanger 123 is subdivided into two contiguous parts 125a, 125b, communicating with each other only near to the short side 123b, opposite short side 123c, from which the plate itself extends.

In accordance with another characteristic of the present invention, each of the two sides 125a, 125b of the inner chamber 125, of each exchanger, is in communication with the outside through respective tubular connectors 126, 127 provided in said exchanger 123, in correspondence with the short side 123c thereof, from which the separator plate 124 projects.

As shall be better seen from the rest of the description, in each exchanger 123, the aforementioned sides 125a, 125b of the chamber 125, respectively constitute the descending portion and the ascending portion of a substantially U-shaped path, for a predetermined heat exchange fluid.

When adapted to form said heat exchange unit 107, in the arrangement described above (FIG. 6), the exchangers 123 have vertical long sides 123a and horizontal short sides 123b, 123c, extending radially in the shell 4; in particular, the side 123c, connected to the relative connectors 126 and 127, constitutes the upper side of each exchanger 123, whereas the side 123b constitutes the lower side in correspondence with which said exchanger is supported inside the shell 4, through the bracket 16 as described above.

For each group of three radially aligned exchangers 123, a duct 128 for feeding-distributing an operating heat exchange fluid, and a collector duct 129, for collecting and discharging said fluid is provided. The duct 128 is connected to the tubular connectors 126 of said exchangers 123 through ducts 128a, whereas the duct 129 is connected to the tubular connectors 127 thereof through ducts 129a.

The feeding duct 128 crosses the shell 4, to be connected, outside of it, to a non-represented source of said operating fluid (for example consisting of boiling water).

The collector duct 129, in the same way as the feeding duct 128, is engaged through the shell 4, to be connected to different applications outside of the reactor 1.

The engagement of the ducts 128 and 129 through the shell 4 is realised using suitable connectors 130 and 131, respectively, provided in the shell at a height close to or coinciding with that of the upper sides 123c of the individual exchangers 123.

With the arrangement described above it is possible to achieve a further important advantage. Indeed, the exchangers 123 can freely expand upwards, where there is no obstacle between them and other parts of the reactor 1, in particular the shell 4.

In this way, it is possible to avoid possible drawbacks of a mechanical type, due to the different thermal expansions of the exchangers and of the shell. These being drawbacks which typically crop up when in the exchangers operating fluids different to the fluids flowing outside of them are used.

Figure 7:
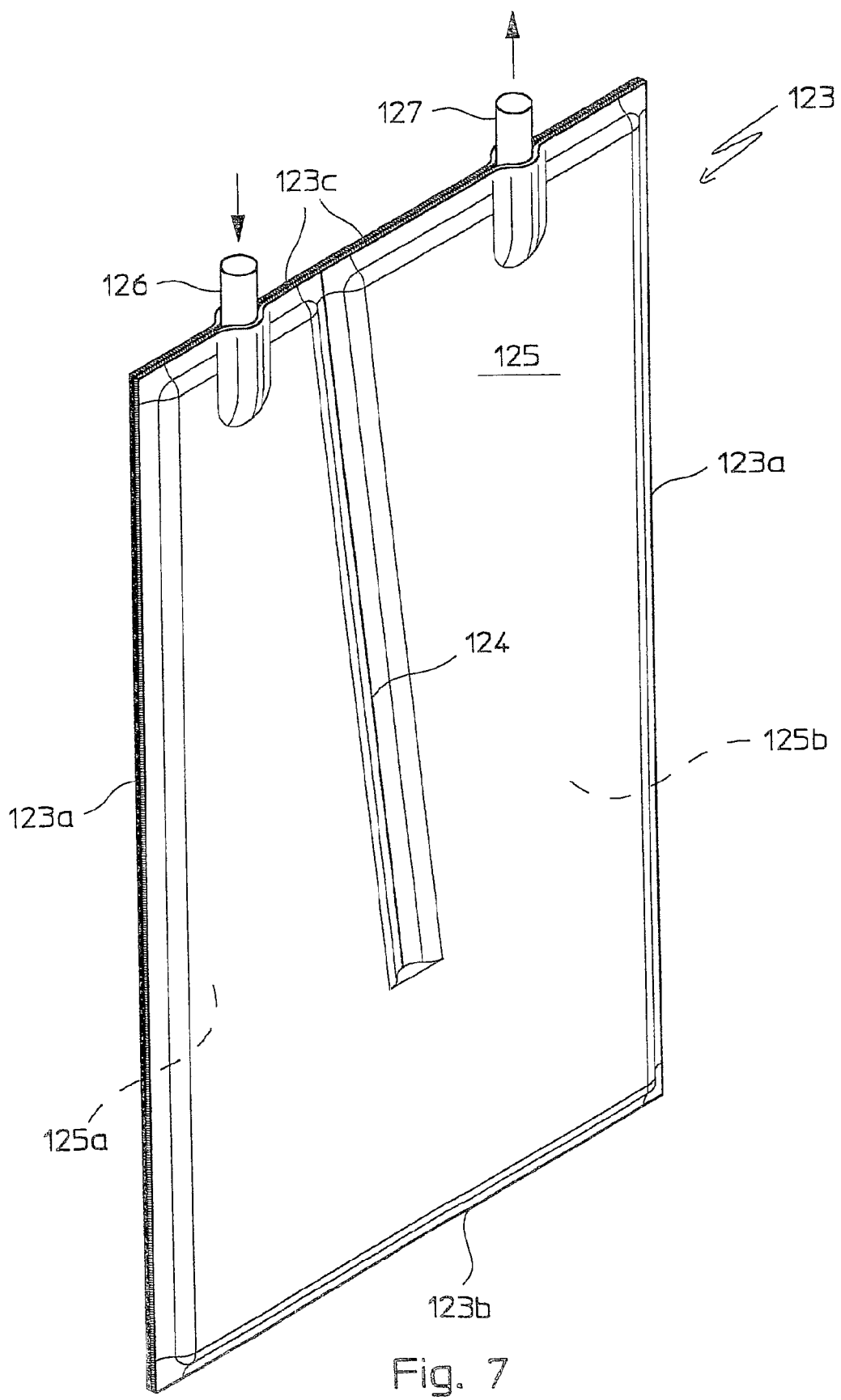
FIG. 7 represents an enlarged perspective view of a detail of the synthesis reactor of FIG. 6.

In FIG. 7 a variant embodiment of the exchanger 123 is represented which is particularly, even if not exclusively, recommended when the operating heat exchange fluid to be used is water. According to this variant, the separator plate 124 extends, inside the chamber 125, in a direction forming a corner with said side 123c of the exchanger 123 (i.e. in an inclined direction with respect to the long sides of the exchanger itself), so as to define in said chamber 125 a U-shaped fluid path, having both a descending portion and an ascending portion with a gradually growing cross-section.

Advantageously, the exchangers 17, 117 and 123 have transversal dimensions such that one can easily, pass through the manhole 13, with which the reactor 1 is equipped.

The advantages achieved by the present invention can be summed up as follows:

it is possible to realise plants for urea production with a much higher capacity than that which has been realised up to now, thanks to the fact that one of the most critical apparatuses from this point of view, the condenser, no longer has the "obstacles" consisting of the presence of the tubular plates;

there is no longer the problem of distributing the urea-carbamate solution in each tube of the tube bundles, nor of guaranteeing that each tube be sufficiently heated or cooled by the fluid outside of it;

the possibility of avoiding possible drawbacks of the mechanical type, due to the different heat expansions of the exchangers and of the shell;

the possibility of easily and quickly defining and replacing the damaged plates or groups of exchangers;

the ease and speed of installation of the condensation units inside the respective shells due to the size of the exchangers: indeed, they easily pass through the manholes normally provided in said shells;

a reduction in the investment costs and simplicity of realisation with respect to the prior art.

The invention thus conceived is susceptible to further variants and modifications all within the reach of the man skilled in the art and, as such, falling within the extent of protection of the invention itself, as defined by the following claims.

The invention claimed is:

1. A plant for urea production from ammonia and carbon dioxide comprising:
   a generally cylindrical synthesis reactor defining a longitudinal axis thereof and a condensation unit positioned inside said reactor, all substantially operating at the same pressure,
   wherein said condensation unit comprises a plurality of flattened plate-shaped essentially rectangular heat exchangers, arranged with long sides parallel to the longitudinal axis of said reactor,
   wherein each of said exchangers comprises a pair of juxtaposed metallic plates, joined together by perimetric welding so as to define a chamber of predetermined width between them,
   wherein at least one of said exchangers is internally equipped with a separator plate, extending from one side of said exchanger, towards a side opposite it and from which said plate is in a predetermined distanced relationship, said plate defining in said chamber a substantially U-shaped fluid path having descending and ascending portions, respectively, in communication with the outside of the exchanger through respective connectors, and
   wherein said separator plate extends in said chamber in a direction forming an angle with said side, for which reason the portions of said fluid path inside the exchanger have a gradually increasing cross-section.

2. The plant according to claim 1, wherein said exchangers have predetermined cross sections of less than the cross sections of a manhole opening arranged in correspondence with a base plate of said reactor.

* * * * *